United States Patent
Rahikkala et al.

(10) Patent No.: US 6,259,527 B1
(45) Date of Patent: Jul. 10, 2001

(54) OPTICAL MEASURING ARRANGEMENT

(75) Inventors: Arvo Rahikkala, Kajanni; Risto J. Heinonen, Vantaa, both of (FI)

(73) Assignee: Metso Field Systems Oy, Helsinki (FI)

( * ) Notice: Subject to any disclaimer, the term of this patent is extended or adjusted under 35 U.S.C. 154(b) by 0 days.

(21) Appl. No.: 09/215,956

(22) Filed: Dec. 18, 1998

(30) Foreign Application Priority Data

Dec. 23, 1997 (FI) .......................................... 974627

(51) Int. Cl.$^7$ .............................. G01N 21/00; G01N 1/10; G01J 5/02
(52) U.S. Cl. ............................ 356/440; 356/246; 250/343
(58) Field of Search .................................. 356/246, 440, 356/436; 250/343

(56) References Cited

U.S. PATENT DOCUMENTS 3,544,798  12/1970  Topol .
5,521,384  5/1996  Lynch ................................. 250/343

FOREIGN PATENT DOCUMENTS 0327353  8/1989  (EP) .

*Primary Examiner*—F. L. Evans
*Assistant Examiner*—Amanda Merlino
(74) *Attorney, Agent, or Firm*—Ladas & Parry

(57) ABSTRACT

The invention relates to an optical measuring arrangement for measuring, particularly for liquid or gaseous substances (103). The measuring arrangement comprises at least one measuring head (104, 106) operating on an optical measuring band, and a measuring head holder (100) comprising a hole (108, 112) for fastening and supporting the measuring head (104, 106). In the hole, the holder (100) comprises an end piece (110) through which the measurement is to be made. On the optical band of the measuring head (104, 106), the end piece (110) is substantially transparent. Furthermore, the end piece (110) separates the measuring head from the substance (103) to be measured disposed in the measuring area (102).

14 Claims, 2 Drawing Sheets

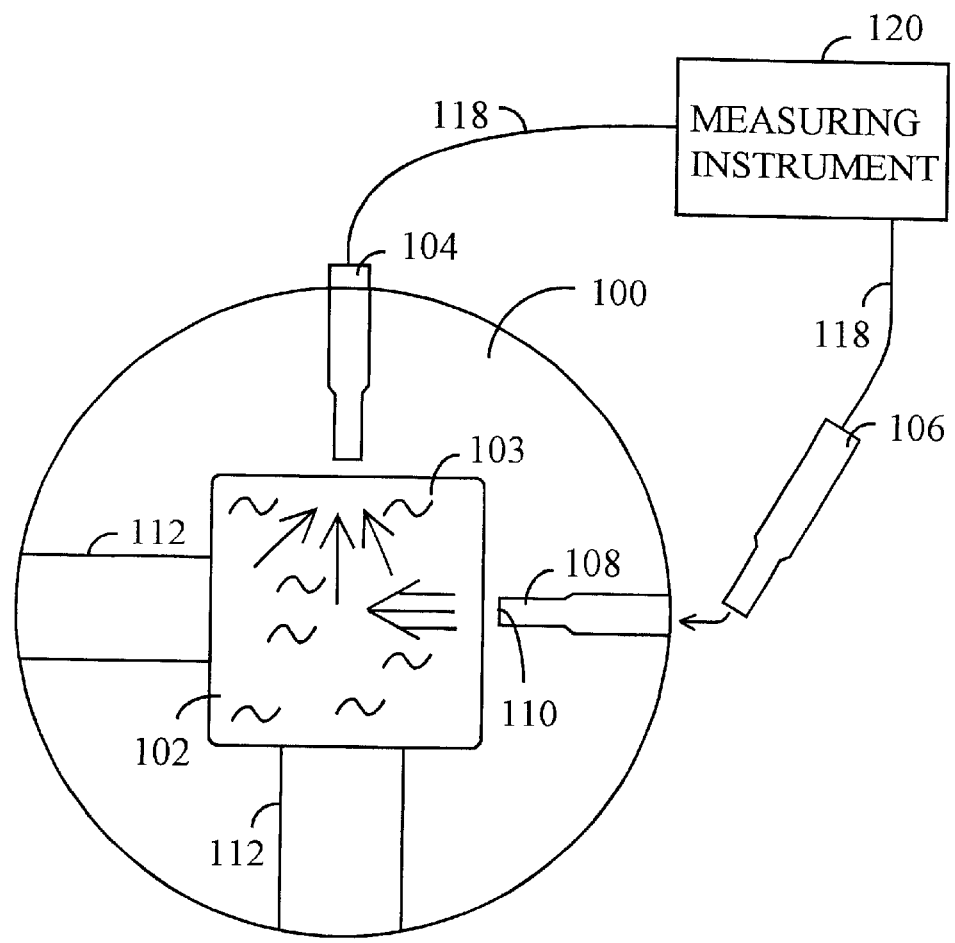
FIG. 1
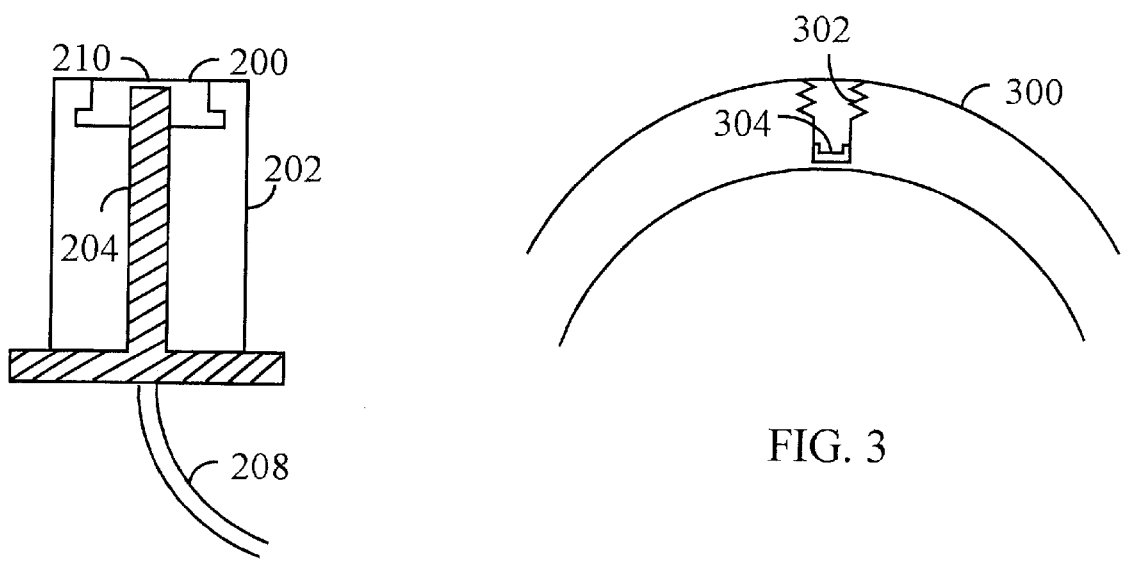
FIG. 2
FIG. 3

OPTICAL MEASURING ARRANGEMENT

BACKGROUND OF THE INVENTION

The invention relates to an optical measuring arrangement for measuring, for particularly liquid or gaseous substances, the arrangement comprising at least one measuring head operating on an optical measuring band, and a measuring head holder comprising a hole for fastening and supporting the measuring head.

FIELD OF THE INVENTION

Liquid and gaseous substances are often measured optically, the wavelength range employed extending from ultraviolet radiation to the infrared range. In known solutions for measuring liquid or gaseous substances, the measuring heads are typically in contact with the substance to be measured. If the substance to be measured is fouling or corrosive, the measuring head works only short periods of time without maintenance. Consequently, the measuring head has to be cleaned or changed. When measurements are made to observe an industrial process, the entire process has to be stopped because of the maintenance of the measuring heads. Such interruptions are inconvenient and costly.

An attempt has been made to solve the problem by coating the measuring heads with protective material, which, however, wears away. In addition, between the measuring head and the rest of the process structure remain at least some rough points, to which solid matter contained in the substance to be measured adhere, thus hampering the optical measuring direction of the measuring head. Furthermore, it is difficult to seal the usually very small measuring head reliably to e.g. a process tube.

BRIEF DESCRIPTION OF THE INVENTION

It is an object of the invention to provide a method, and an equipment for implementing the method, to solve the above problems and to protect the measuring head against the fouling and/or damage caused by the substance to be measured.

This is achieved by a measuring arrangement of the type presented in the introduction, characterized in that the holder comprises for the hole an end piece, through which the measurement is to be performed; which is substantially transparent on the optical measuring band of the measuring head; and which separates the measuring head from the substance which is to be measured and which is disposed in the measuring area.

The system of the invention provides a plurality of advantages. The fouling and breaking of the measuring head can be easily prevented by protecting it from the influence of the substance to be measured. At the same time accumulation of solid matter hampering the optical operation is prevented at the measuring point, since the area of the measuring head is as even as the surrounding area.

BRIEF DESCRIPTION OF THE DRAWINGS

In the following the invention will be described in greater detail in connection with preferred embodiments with reference to the attached drawings, in which FIG. 1 shows a general measuring instrument arrangement, FIG. 2 shows a measuring head and a measuring head holder, FIG. 3 shows a solution for fastening the measuring head and an arrangement for the optics.

DETAILED DESCRIPTION OF THE INVENTION

Figure 4:
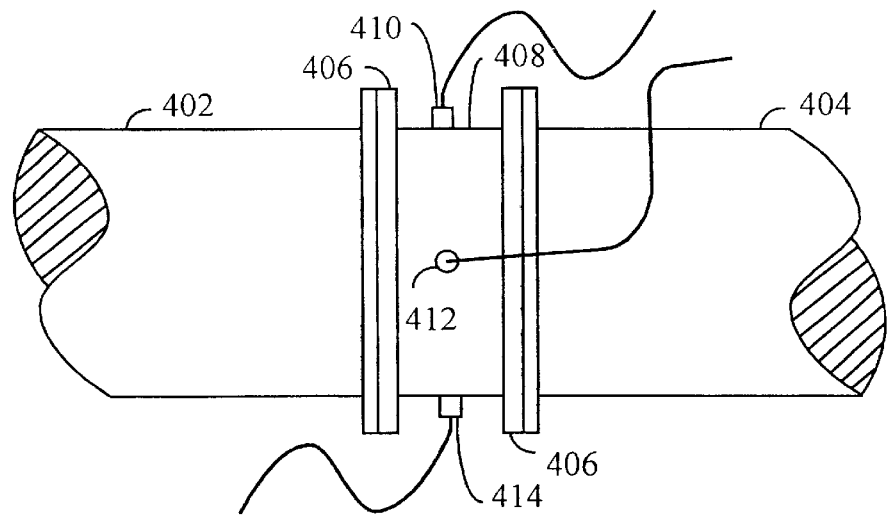
FIG. 4 shows a measuring arrangement in a tube.

The solution of the invention is suitable for optical measurements, particularly for optical measurements of liquid and gaseous substances.

The measuring arrangement of FIG. 1 comprises a measuring head holder 100, a measurement orifice 102, a first measuring head 104, a second measuring head 106, a hole for the measuring head 108, and an end 110 in the hole 108. FIG. 1 also shows an alternative hole type 112, fibers 118 associated with the measuring heads 104 and 106, and a measuring instrument 120.

The measuring arrangement operates e.g. as follows (the hole 112 is ignored in this example). The measuring instrument 120 preferably comprises an optical power source, which transmits ultraviolet radiation, visible light or infrared radiation on a broad or narrow band as a continuous or discontinuous spectrum. Let the measuring head 106 be a transmitter measuring head disposed in the hole 108 as shown by the arrow. The measuring instrument 120 transmits optical radiation along the fiber 118 to the measuring head 106. The measuring head 106 then transmits the optical radiation further through the end 110 to the measurement orifice 102, which is assumed to contain liquid or gaseous substance to be measured. In FIG. 1, at least the end 110 can be considered to be an end piece. On the side of the measurement orifice 102, the end area of the measuring head 106 is completely even, since the measuring head 106 does not extend into the measurement orifice. This substantially lessens wear and fouling of the measuring head 106. The substance 103 to be measured causes optical radiation to scatter (arrows), whereby the measuring head 104 serving as the receiving measuring head receives scattered radiation through the end 110. The optical power propagates further along the fiber 118 to the measuring instrument.

As a measuring arrangement, the above is a completely typical solution, except that the measuring heads 104 and 106 do not extend to the measurement orifice 102 and are consequently not in direct contact with the substance 103 to be measured. The measuring heads 106 and 104 are separated from the measurement orifice 102 by a thin end wall 110 disposed in the hole 108 of the measuring head holder and made from the same material as the rest of the holder material in this example, the end piece 110 and the rest of the holder thus forming one solid piece. Typically, the end wall 110 has to be quite thin, since the material of the measuring head holder 100 may powerfully attenuate optical radiation. As is known, optical transmission is defined as follows:

$$P = P_0 e^{-\alpha l}, \qquad (1)$$

wherein $P_0$ is transmitted power, P is received power, α is neper, a is the attenuation coefficient and l is the travel length of optical power. Formula (1) shows that when end materials with a high attenuation coefficient α are used, the end 110 should be quite thin, i.e. a high attenuation can be compensated for by the thickness of the end 110. This way the end 110 can be made substantially transparent. Materials suitable for the end piece include Teflon, whereby the thickness of the end 110 can be e.g. 0.3 mm. No given measurement or shape is essential to the invention; what is essential is the surprising understanding that the measuring heads 104 and 106 can be efficiently separated from the substance 103 to be measured. Once the measuring heads 104 and 106 have been separated from the substance to be measured, the measuring heads 104 and 106 are protected against problems caused by the substance to be measured, such as fouling, wear and corrosion. The transmitter measuring head 106 can also be a known light-transmitting component, i.e. a led, laser or lamp. The receiver measuring head 104, in turn, can also be an opto-electric detector, obvious to a person skilled in the art. In this case an electric conductor instead of the fiber 118 is used between the measuring heads 104 and 106 and the measuring instrument 120.

FIG. 2 shows an alternative solution for the measuring head holder, comprising a holder 202, a measuring head 204, an optical fiber 208 and an end piece 210. This holder solution is suitable for use in the hole 112 of FIG. 1, for example. The holder comprises an end piece 200, separated from the rest of the holder. This end piece 200 can be of the same material or some other material than the rest of the holder material. In other words, the main material of the holder can be e.g. metal, and the end piece 200 can be of plastic. Since the end piece 200 is larger than the measuring head 204, the end piece 200 can be easily fastened and sealed to the rest of the holder 202 structure. Consequently, FIG. 2 emphasizes the inventive feature, i.e. that in prior art solutions the measuring head, which is typically very small, has to be sealed firmly against the holder. As is well known in the art, it is difficult to seal a small part, but the inventive solution avoids sealing small parts.

FIG. 3 illustrates a preferred manner of fastening the measuring head to a holder 300. In this example, the fastening is carried out by a thread 302. FIG. 3 also shows the preferred feature of the invention, i.e. that a component 304 affecting the optical characteristics is disposed in the hole intended for the measuring head. The component 304 can be e.g. a lens, an optical polarization filter or a band filter.

FIG. 4 shows an application of the inventive solution in a tube system. The solution comprises a first tube 402, a second tube 404, a holder side 406, a holder 408 and measuring heads 410 to 414. The tube 402 and 404 is e.g. a metal tube. This solution employs advantageous pigtailed measuring heads 410 to 414, whose holder 408 is of the shape of a tube, the dimensions of the holder, particularly tubular length, being determined according to the sizes of the measuring heads 410 to 414, the holder naturally being somewhat larger than the measuring heads. Since the holder 408 is tubular, it comprises a similar hole in the middle as does the tube comprising the first tube 402 and the second tube 404. The hole in the middle of the holder is a measurement orifice as in FIG. 1. The measuring heads 410 to 414 are tightly sealed at their sides 406 to the ends of the tube 402 and 404.

Figure 5:
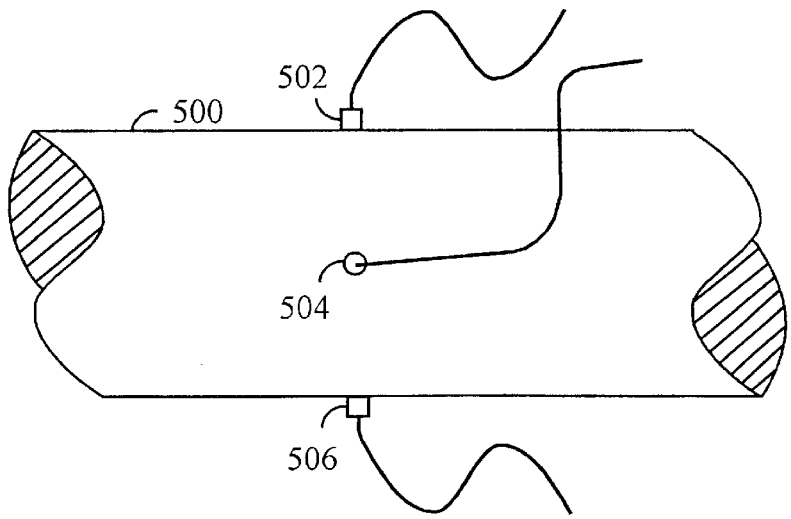
FIG. 5 shows a measuring arrangement in a tube.

FIG. 5 shows a solution similar to that of FIG. 4. The difference in this measuring arrangement is that the tube 500 itself constitutes the holder of measuring heads 502 to 506. In other words, the measuring heads 502 to 506 have holes in the tube 500, which extend close to the hollow core of the tube 500, but the measuring heads 502 to 506 are separated from the hollow interior of the tube by a thin end layer 210 as is illustrated in FIG. 2. That is, the holder of the measuring heads 502 to 506 is preferably of the same material as the tube 500 and a fixed part of the tube.

Should the tube 500 in FIG. 5 be of a different material (e.g. of a non-transparent material, such as metal) than the end of the holder, the measuring head holders resemble those in FIG. 2, and in this case the reference numbers 502 to 506 refer to holders according to FIG. 2, the holders being fastened to holes disposed in the tube 500 and extending through the wall.

Figure 6:
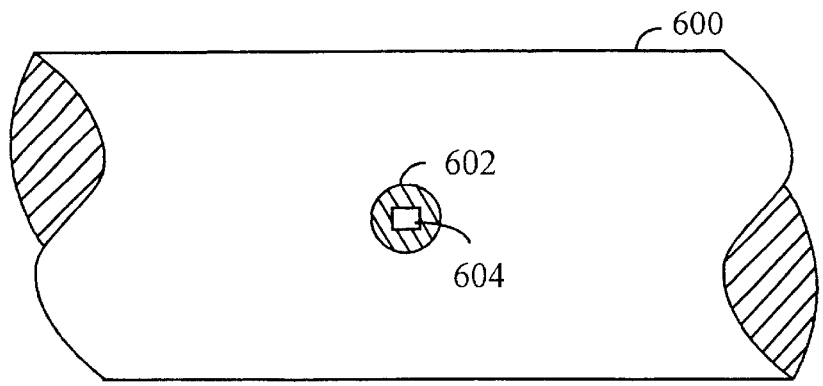
FIG. 6 shows the definition of an orifice.

FIG. 6 shows a feature of the inventive solution. The optical operation of the measuring head and, consequently, the entire measurement process, can be affected by changing the optical orifice of the measuring head. In the inventive solution the optical orifice 604 can be arranged by painting a frame 602 for the orifice at the end of the hole of the measuring head holder 600. The painting can be disposed in the hole against the measuring head protected from the effects of the substance to be measured, or at the hole in the end piece in contact with the substance to be measured.

The measuring arrangement is suitable for use preferably in the wood-processing industry, whereby the substance 103 to be measured is preferably mainly a water-based wood fiber suspension. The suspension can also be e.g. fine rock material, such as kaolin or talcum, mixed with water or another liquid. The substance to be measured can also be a corrosive or dissolving chemical, such as an alkali or an acid. White and green liquor are examples of corrosive chemicals. The features measured from the substances include concentration, opacity, impurity and flow. The inventive solution is also applicable to the chemical, pharmaceutical and mining industries, not being, however, restricted thereto. The material of the holder and the end area 200, in particular, can be different kind of plastic and glass. The measuring heads and the holder can be fastened to the tube e.g. by any fastening manner obvious to a person skilled in the art.

Even though the invention has been explained in the above with reference to the example in accordance with the accompanying drawings, it is obvious that the invention is not restricted thereto but can be modified within the scope of the inventive idea disclosed in the attached claims.

What is claimed is:

1. In a paper or pulp processing apparatus having an optical measuring arrangement having at least one measuring head operating on an optical measuring band, and a holder comprising a surface and a hole for fastening and supporting the measuring head at the surface, the improvements comprising:

an end piece through which the measurement is to be performed, the end piece being substantially transparent on the optical measuring band of the measuring head and separating the measuring head from the substance to be measured at the surface;

the holder and end piece being a single piece all of the same material; and the surface being even.

2. A measuring arrangement as claimed in claim 1, wherein the end piece is larger than the measuring head.

3. A measuring arrangement as claimed in claim 1, wherein the end piece is of a material, which permeates optical measuring band radiation poorly and has a high optical power attenuation coefficient, and the end piece disposed against the measuring head is made sufficiently thin so that the end piece is substantially transparent to the optical radiation of the measuring band.

4. A measuring arrangement as claimed in claim 1, wherein the measuring head is fastened by a threading to the holder.

5. A measuring arrangement as claimed in claim 1, wherein a component affecting the optical characteristics of the measuring head is mounted in a recess in the end piece.

6. A measuring arrangement as claimed in claim 1, wherein, when a liquid or gaseous substance is measured in a tube, the holder is of the shape of a tube, its length in the direction of the tube being determined according to the measuring head, in the middle of the holder is arranged a hole, in which the liquid or gaseous substance is to be measured, the measuring head holder is tightly seamed at its sides between the ends of the two tubes.

7. A measuring arrangement as claimed in claim 1, wherein, when a liquid or gaseous substance is measured in a tube, the holder is of the same material as the tube and the holder is a solid part of the tube.

8. A measuring arrangement as claimed in claim 1, wherein, for the measurement, an optical orifice is formed by painting an orifice of the desired size in the end piece.

9. A measuring arrangement as claimed in claim 1, wherein the substance to be measured is a water-based suspension.

10. A measuring arrangement as claimed in claim 1, wherein the substance to be measured is a corrosive substance.

11. A measuring arrangement as claimed in claim 10, wherein the substance to be measured is white or green liquor.

12. A measuring arrangement as claimed in claim 1, wherein the holder is a tube having the surface inside which the substance to be measured flows.

13. In a paper or pulp processing apparatus having an optical measuring arrangement having at least one measuring head operating on an optical measuring band, a holder having a surface and a hole for supporting the measuring head at the surface, and an end piece for the hole through which a measurement is to be performed, the improvements wherein:

the end piece is substantially transparent on the optical measuring band of the measuring head;

the surface separates the measuring head from a substance to be measured;

the holder and end piece are a single piece all of the same material; and the surface is even.

14. A measuring arrangement as claimed in claim 13, wherein the holder is a tube having the surface inside which the substance to be measured flows.

* * * * *